(12) United States Patent
Grasteau et al.

(10) Patent No.: US 11,340,211 B2
(45) Date of Patent: May 24, 2022

(54) SERUM COLOR AS BIOMARKER OF DIGESTIVE EFFICIENCY OF POULTRY

(71) Applicants: INSTITUT NATIONAL DE RECHERCHE POUR L'AGRICULTURE, L'ALIMENTATION ET L'ENVIROMENT, Paris (FR); UNIVERSITE DE TOURS, Tours (FR)

(72) Inventors: Sandrine Grasteau, Marolles les Saint Calais (FR); Elisabeth Duval, Montlouis/Loire (FR); Stéphane Beauclercq, Tours (FR)

(73) Assignees: UNIVERSITE DE TOURS, Tours (FR); INSTITUT NATIONAL DE RECHERCHE POUR LAGRICULTURE, L'ALIMENTATION ET L'ENVIRONNEMENT, Paris (FR)

( * ) Notice: Subject to any disclaimer, the term of this patent is extended or adjusted under 35 U.S.C. 154(b) by 0 days.

(21) Appl. No.: 17/275,987

(22) PCT Filed: Sep. 13, 2019

(86) PCT No.: PCT/EP2019/074527
§ 371 (c)(1),
(2) Date: Mar. 12, 2021

(87) PCT Pub. No.: WO2020/053409
PCT Pub. Date: Mar. 19, 2020

(65) Prior Publication Data
US 2022/0026410 A1    Jan. 27, 2022

(30) Foreign Application Priority Data
Sep. 14, 2018 (EP) .................................. 18306198

(51) Int. Cl.
*G01N 33/48* (2006.01)
*G01N 33/49* (2006.01)
(Continued)

(52) U.S. Cl.
CPC ............. *G01N 33/49* (2013.01); *A01K 43/00* (2013.01); *A23K 50/75* (2016.05); *G01N 21/3103* (2013.01)

(58) Field of Classification Search
CPC .... G01N 33/49; G01N 15/05; G01N 15/1434; A61B 5/14532; A61B 5/1455
(Continued)

(56) References Cited

U.S. PATENT DOCUMENTS

2015/0037439 A1*   2/2015   Khirug .................. A23K 50/80
                                                        424/725

FOREIGN PATENT DOCUMENTS

WO         2016065359 A1     4/2016

OTHER PUBLICATIONS

Abrar, H., et al., 2015, Carotenoid content in organically produced wheat: relevance for human nutritional health on consumption, Int. J. Environ. Res. Public Health 12, 14068-14083.
(Continued)

*Primary Examiner* — Md M Rahman
(74) *Attorney, Agent, or Firm* — Arrigo, Lee, Guttman & Mouta-Bellum LLP

(57) ABSTRACT

The invention relates to an in vitro method for evaluating digestive efficiency (DE) of poultry, in particular chickens, by measuring color of a sample of liquid fraction of blood of said poultry.

12 Claims, 2 Drawing Sheets

(51) Int. Cl.
*A01K 43/00* (2006.01)
*A23K 50/75* (2016.01)
*G01N 21/31* (2006.01)

(58) Field of Classification Search
USPC .......................................................... 356/39
See application file for complete search history.

(56) References Cited

OTHER PUBLICATIONS

Bastianelli, D., et al, 2010, Prediction of the chemical composition of poultry excreta by near infrared spectroscopy, Near Infrared Spectrosc, 18, 69-77.

Beauclercq S., et al., 2018, Relationships between digestive efficiency and metabolomics profiles of serum and intestinal contents in chickens, Scientific Reports, 8, 6678.

Bourdillon, A., et al ., 1990, European reference method for the in vivo determination of metabolisable energy with adult cockerels: reproducibility, effect of food intake and comparison with individual laboratory methods, Br. Poult. Sci. 31,557-65.

De Verdal, H., et al., 2013, Reducing the environmental impact of poultry breeding by genetic selection, J. Anim. Sci., 91, 613-622.

Garcia, V., et al., 2007, Effects of xylanase and antibiotic supplementations on the nutritional utilisation of a wheat diet in growing chicks from genetic D+ and D- lines selected for divergent digestion efficiency, Animal 1, 1435-1442.

Groeneveld, E., et al., 2010, VCE user's guide and reference manual version 6.0.

Mignon-Grasteau, S., et al., 2004, Heritability of digestibilities and divergent selection for digestion ability in growing chicks fed a wheat diet, Poult Sci, 83, 860-867.

Neumaier, A., and E. Groeneveld, 1998, Restricted maximum likelihood estimation of covariances in sparse linear models, Genet. Sel. Evol. 1, 3-26.

Rodriguez-Amaya, D. B, 2001, A guide to carotenoid analysis in foods, ILSI Press, Washington D.C., U.S.A.

Stone, H. A., Urban, W. E., and W. M. Collins. 1971. Blood carotenoid concentration, an estimate of its heritability and genetic relationship to body weight in chicken. Poult Sci. 6:1859-1862.

Surai, P. F., et al., 2001, Carotenoids in avian nutrition and embryonic development. 1. Absorption, availability and levels in plasma and egg yolk, J. Poult, Sci. 38, 1-27.

Washburn, K.W., and M. D. Ruff, 1978, Genetic variability of carotenoid content in commercial broilers, Arch. Geflugelkd, 42, 193-196.

Welch, B.L., 1947, The generalization of Student's problem when several different population variances are involved, Biometrika 34, 28-35.

Faure, H., et al., 1999, Les caroténoïdes : 1. Métabolisme et physiologie, Ann. Biol. Clin, 57, 169-183.

Beauclercq S., et al., 2018, Does lipidomic serum analysis support the assessment of digestive efficiency in chickens, Poultry Science, 1-7.

* cited by examiner

SERUM COLOR AS BIOMARKER OF DIGESTIVE EFFICIENCY OF POULTRY

FIELD OF THE INVENTION

The present invention relates to an in vitro method for evaluating digestive efficiency (DE) of poultry, in particular chickens, by measuring color of a sample of liquid fraction of blood of said poultry.

BACKGROUND OF THE INVENTION

The feedstuffs used in poultry diets are becoming increasingly diverse, in order to limit the competition with human food by using by-products of cereals as well as to include more local resources in diets and thus limit dependency on importations, e.g. for soybean in Europe. These alternative feedstuffs are, however, often of lower and more variable quality than the traditional corn and soybean diets. Consequently, the digestive efficiency (DE) of chickens fed with these new and less optimal diets is becoming a more important component of feed efficiency than before. Improving digestive efficiency, and in turn feed efficiency, is thus a critical element of economic profitability and of the environmental impact of poultry production. And it bolstered the interest in genetic selection for digestive efficiency, a component of feed efficiency, assessed by apparent metabolisable energy corrected to zero nitrogen retention (AMEn).

Thanks to the development of near-infrared spectroscopy technology (NIRS), the feasibility of large-scale measurements of digestive efficiency has been greatly improved compared to former chemical analyses. It has made it possible to perform a genetic experiment on this trait, during which we showed that digestive efficiency was heritable and could be used as a criterion of selection (Mignon-Grasteau et al., 2004). However, the preparation of feces samples from a large number of animals (poultry) is still time-consuming. Moreover, the total collection of feces involves rearing animals (poultry) in individual cages for the duration of the balance trial, which is detrimental to their welfare.

So there is still a need of having valuable biomarkers of digestive efficiency that are fast to measure and available from floor-reared animals (poultry), to improve the efficiency of selection in real rearing conditions and with respect to animal welfare.

The Applicant showed in the present invention that serum absorbance at 492 nm could be used as an indirect criterion for selecting digestive efficiency.

SUMMARY OF THE INVENTION

A first object of the invention is an in vitro method for evaluating digestive efficiency (DE) of poultry, in particular chickens, by measuring color of a sample of liquid fraction of blood of said poultry.

The invention also concerns the use of the in vitro method according to the invention for selecting poultry, in particular chickens, having an improved digestive efficiency (DE).

Another object of the invention is the use of the in vitro method according to the invention for selecting feedstuffs or diets and/or producing feedstuffs or diets adapted and/or optimized for poultry, in particular for chickens.

Another object of the invention is the use of color of a sample of liquid fraction of blood, in particular plasma sample or serum sample, preferably serum sample of poultry, as an indirect criterion for selecting digestive efficiency (DE) of poultry, in particular digestive efficiency (DE) of chickens.

The present invention is very simple and rapid:
It performs a single blood test on the animal,
The amount of sample of liquid fraction of blood, in particular serum sample needed for analysis is low (200 µL), which limits the amount of blood to be taken from animals, and
It performs a colorimetric measurement on sample of liquid fraction of blood, in particular serum sample.

And the main advantages of this new technique are:
poultry no longer have to be placed in individual cages and are handled once,
the time required for blood sampling and colorimetric measurement is extremely low, then several hundred animals can be measured in one day,
the staff required for this technique is reduced,
this technique does not require the purchase of laboratory consumables or indigestible markers, and uses measurement equipment at a cost that is much lower than that used in previous methods.

DETAILED DESCRIPTION OF THE INVENTION

Figure 1:
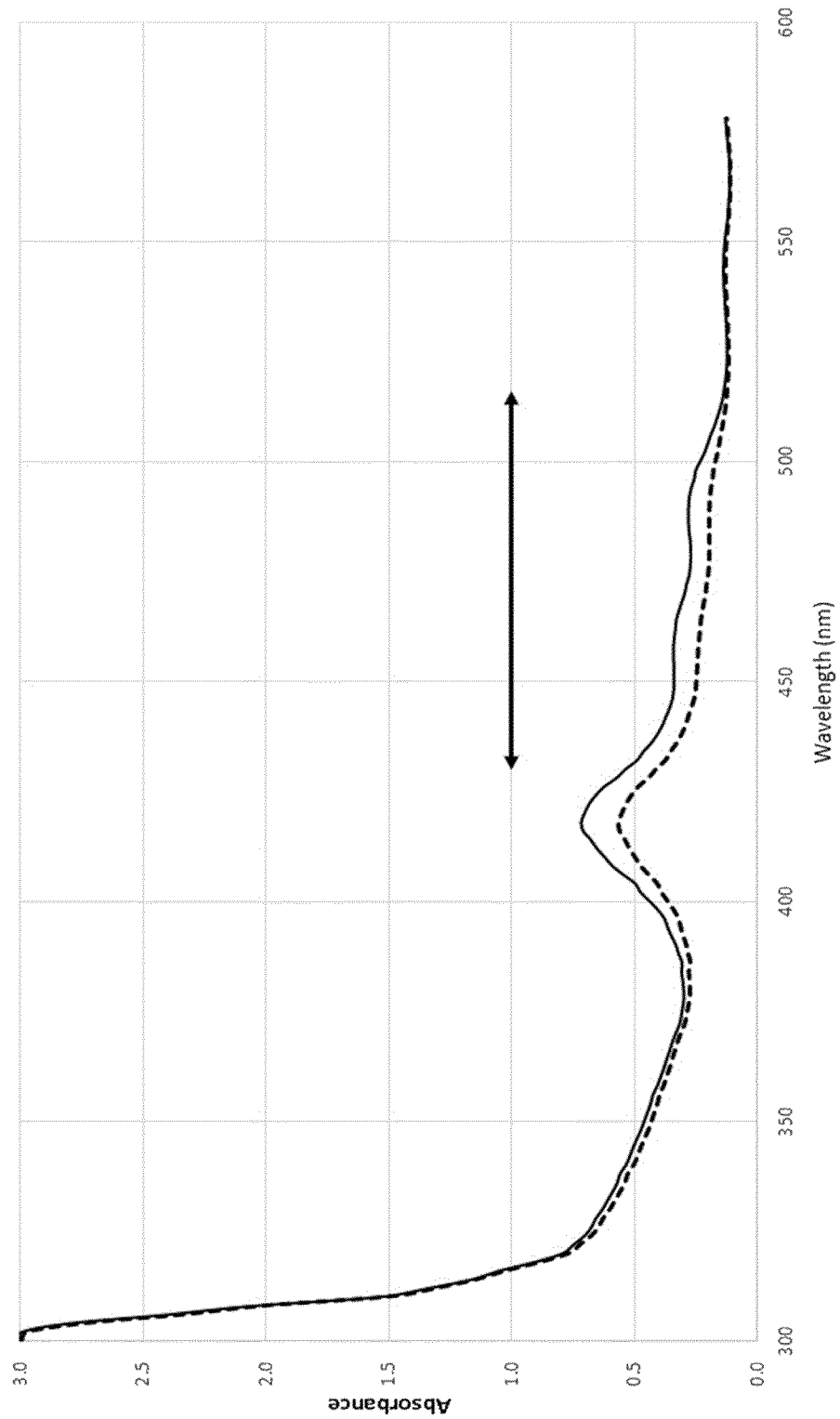
FIG. 1. Absorbance of serum sample between 300 and 578 nm in experiment 1 for a line of chickens with high digestive efficiency D+ (solid line) and a line of chickens with low digestive efficiency D− (dashed line) birds. The arrow indicates the zone for which the difference between the two lines is significant.

The present invention relates to an in vitro method for evaluating digestive efficiency (DE) of poultry, in particular chickens, by measuring color of a sample of liquid fraction of blood of said poultry.

By 'liquid fraction of blood' according to the invention, it means the non-cellular fraction of the blood. Indeed, the blood is a body fluid in human and other animals, composed of blood cells (red blood cells, white blood cells and platelets) suspended in a blood's liquid medium.

The present invention focuses on the blood's liquid medium, ie liquid fraction of blood.

When blood is fractionated by centrifugation, three layers can be seen: Plasma (upper, yellow layer), buffy coat (middle, thin white layer) and erythrocyte layer (bottom, red layer).

Blood plasma represents about 55% of blood, and is the blood's liquid medium, which by itself is straw-yellow in color. It is essentially an aqueous solution containing 92% water, 8% blood plasma proteins, and trace amounts of other materials. It also contains blood-clotting factors (to facilitate coagulation).

The term 'serum' refers to plasma from which the clotting proteins have been removed.

In a particular embodiment of the invention, the sample of liquid fraction of blood is a plasma sample or a serum sample.

In a particular and preferred embodiment, the sample of liquid fraction of blood is a serum sample.

In a particular embodiment, poultry are selected in the group consisting of chicken, hen, turkey, goose, duck, guinea fowl, quail, and pigeon.

In a particular and preferred embodiment, said poultry is chicken.

In a particular and preferred embodiment of the invention, the sample of liquid fraction of blood is a serum sample of chicken.

The 'digestive efficiency' (DE) according to the invention is a component of feed efficiency, usually assessed by apparent metabolisable energy corrected to zero nitrogen retention (AMEn).

The sample of liquid fraction of blood, in particular serum sample, may be collected at different times (ages of the poultry).

In a particular embodiment, the sample of liquid fraction of blood, in particular serum sample of chicken is collected between 21 to 25 days, preferably between 23 to 25 days. Indeed, differences linked to DE are expected to be maximal around at this age, according to inventors' studies on serum samples of chickens.

In a particular embodiment, the plasma samples are collected with the following steps:
  The blood sample is sampled, in particular at 3 weeks, at the occipital sinus of poultry, in particular chicken and collected on dry tube with anticoagulant agent;
  The collected sample containing an anti-coagulant agent is centrifuged for 10 minutes at 3000 g;
  The supernatant (ie plasma sample) is taken with a pipette.

As non-limitative examples of anti-coagulant agents, mention may be made of EDTA, heparin salts, and sodium citrate.

In another particular and preferred embodiment, the serum samples are collected with following steps:
  The blood sample is sampled, in particular at 3 weeks, at the occipital sinus of poultry, in particular chicken and collected on dry tube;
  The collected sample is rested at room temperature for 15 minutes until coagulation;
  The coagulated blood is centrifuged for 10 minutes at 3000 g;
  The supernatant (ie serum sample) is taken with a pipette.

The 'color of a sample' according to the invention is a specific feature of a poultry; in the context of the invention, it is influenced by pigments contained in the food (diet) and the digestive efficiency (DE) of the poultry.

In particular, the color is related to absorbance of said sample by spectrophotometry.

The principle is the following: an illuminated sample (solution) in white light appears colored if it absorbs a part of the radiations of the white light. The color of the sample (solution) is then that of the transmitted radiations, that is to say the complementary color of the absorbed color. The spectrum of colored light has dark absorption bands that depend on the nature of the sample (solution). For each radiation of wavelength λ, the proportion of light absorbed by the sample (solution) is measured by its absorbance A (λ). So the absorbance is a physical quantity that reflects the ability of a sample (solution) to absorb radiation.

The absorbance depends essentially on two parameters: the concentration of the sample (solution) and the wavelength of light which goes through the sample (solution).

The absorbance is therefore a quantity related to the intensity of the light of wavelength A absorbed in sample (solution). And there is a wavelength for which the absorbance is maximum. The color of the sample (solution) then corresponds to the complementary color.

The wavelengths of the visible spectrum are between 400 and 700 nm.

In a particular embodiment, the color of a sample of liquid fraction of blood, in particular serum sample, preferably serum sample of chicken, according to the invention, is measured by absorption spectrum between 400 and 520 nm, preferably between 430 and 516 nm, more preferably between 460 and 500 nm and even more preferably at 492 nm wavelength.

The Applicant demonstrated that, in particular for serum samples of chickens, the most significant difference was found in particular at 492 nm, which corresponds to the region of carotenoid absorption, especially lutein and zeaxanthin which are the major carotenoids present in cereal grains, particularly wheat. Moreover, as lutein and zeaxanthin are better absorbed by chickens than other carotenoids present in this spectral zone, such as γ-carotene, astaxanthin or cryptoxanthin, we can expect that this peak of absorbance at 492 nm is likely to correspond to lutein and zeaxanthin.

In a particular embodiment, for large scale evaluation or screening, several samples of poultry may be placed in well plates, and their absorbance is measured by an automate spectrophotometer. So the present invention also related to in vitro method for evaluating and/or screening DE by measuring color of samples of liquid fraction of blood, wherein said samples of liquid fraction of blood, in particular serum samples, preferably serum samples of chickens, are placed in well plates (one sample per well) and the absorption spectrum (of each sample) is measured with a spectrophotometer.

In a particular embodiment, the measure of color of a sample of liquid fraction of blood, in particular color of serum sample is realized by the following steps:
  Deposit of 200 μL of sample of liquid fraction of blood, in particular serum sample, in the wells of the plate (one sample per well), in according to a pre-defined deposition plan;
  Acquire an absorption spectra using a spectrophotometer between 300 and 600 nm (2 nm steps);
  Measure of the absorbance of said samples (one absorbance per sample) between 400 and 520 nm, preferably between 430 and 516 nm, more preferably between 460 and 500 nm and even preferably at 492 nm wavelength, according to the spectrophotometer notice, preferably in triplicate; and
  Save spectrometry results for further analysis of variance.

In a preferred embodiment, the plate is a transparent 96 well plates.

In a particular and preferred embodiment, the samples of liquid fraction of blood are serum samples, preferably serum samples of chickens and the absorption spectrum is measured at 492 nm wavelength.

A peak of absorbance of a sample of liquid fraction of blood, in particular serum sample and preferably serum sample of chicken, in particular at 492 nm wavelength, is suspected to correspond to a higher concentration of carotenoids absorbed by the poultry.

The invention also concerns the use of the in vitro method according to the invention for selecting poultry, in particular chickens, having an improved digestive efficiency (DE).

It means that selective breeding of poultry with higher values of absorbance in sample of liquid fraction of blood, in particular serum sample, in particular at 492 nm, will lead to a higher value of digestive efficiency (assessed by AMEn).

In a particular embodiment, the in vitro method of the invention comprises a step of selecting poultry, in particular chickens, having higher values of absorbance in plasma sample or serum sample, preferably serum sample, at 492 nm wavelength.

The invention also concerns the use of the in vitro method according to the invention for selecting feedstuffs or diets and/or producing feedstuffs or diets adapted and/or optimized for poultry, in particular for chickens.

In particular, the in vitro method of evaluation of digestive efficiency (DE) of a poultry, which is fed by feedstuffs or diets to be tested, may help to select feedstuffs or diets which are adapted and/or optimized for better digestive efficiency (DE).

By 'adapted and/or optimized' for poultry, it means feedstuffs or diets whose composition are adapted for nutrition of poultry and/or even optimized, meaning expected to be better digested by poultry.

Another object of the invention is the use of color of a sample of liquid fraction of blood, in particular plasma sample or serum sample, preferably serum sample of poultry, as an indirect criterion for selecting digestive efficiency (DE) of poultry, in particular digestive efficiency (DE) of chickens.

The invention will now be illustrated by the non-limitative following examples.

EXAMPLES

The serum color of two lines of chickens divergently selected for high or low digestive efficiency when fed with a wheat-based diet were compared. Color was assessed by the absorbance of the serum between 300 and 578 nm. Color differed between the two lines between 430 and 516 nm, which correspond to the absorption zone of carotenoids such as lutein and zeaxanthin.

Then the heritability of serum color measurements as well as their genetic correlations with digestive efficiency were evaluated.

Materials and Methods
Animals (Poultry)

The terms 'animal', 'poultry', 'bird' or 'chicken' are used interchangeably in the rest of the description of the examples.

All animal care and experimental procedures reported in this paper were in accordance with French and European regulations concerning animal experimentation. The experimental units in which the birds (chickens) were kept are registered by the Ministry of Agriculture with license numbers C-37-175-1 and A-17-661 for animal experimentation. All the procedures applied to the birds (chickens) during these experiments are covered by agreements 00885.02, 2015121516442084-3202 and 2015040111006849 delivered by the French Ministry of Research after approval by the ethics committees C2EA-19 and C2EA-84.

The data used in this study come from two successive experiments on divergent lines of chickens selected for high (D+) or low (D−) digestive efficiency. The initial population is a commercial medium-growing broiler, reaching 2 kg at 7 weeks. During the first 8 generations, the birds were fed a difficult-to-digest diet that included 55% of Rialto wheat (Mignon-Grasteau et al., 2004), a hard and viscous wheat variety. Breeders were selected for digestive efficiency using the AMEn measured during a balance trial at 3 weeks. The two lines were then reproduced without selection for AMEn during the 9 following generations. At generation 20, the selection process was restarted with the same criterion of selection.

Experiment 1. At generation 20, it was not possible to obtain new Rialto wheat anymore. A preliminary test was performed to replace it with another diet containing another variety of wheat and rye, to mimic the effects of Rialto. The composition of the two diets is given in Table 1.

TABLE 1

Composition of diets and elementary statistics on AMEn at 3 weeks for D+ and D− lines (mean ± standard deviation)

| Ingredient | Initial diet including Rialto wheat | Alternative diet without Rialto wheat |
| --- | --- | --- |
| Corn | | 4.31 |
| Wheat | 55.00 | 51.40 |
| Rye | | 5.00 |
| Rapeseed oil | 8.00 | |
| Soybean oil | | 3.00 |
| Palm oil | | 3.00 |
| Soybean cake 48 | 33.24 | 28.87 |
| Calcium carbonate | 1.19 | 1.14 |
| Bicalcic Phosphate | 1.55 | 1.99 |
| Salt | 0.35 | 0.30 |
| Vitamins-Minerals | 0.50 | 0.40 |
| DL Methionine | 0.12 | 0.26 |
| HCL Lysine | | 0.21 |
| Threonine | | 0.07 |
| Anticoccidial | 0.05 | 0.05 |
| Crude Proteins (%) | 21.0 | 20.0 |

The birds (chickens) were reared on the floor for 16 days and then transferred to individual cages. A balance trial was done between 23 and 25 d on 20 birds per line and per diet. The birds were weighed at 23 and 25 days (23 and 25 d). A total collection of feces was done during this time, as suggested by Bourdillon et al. (1990). Feces were freeze-dried and analyzed with NIRS to obtain AMEn values as in Bastianelli et al. (2010).

At the end of the balance trial (25 d), the animals fed with the Rialto diet were blood sampled at the occipital sinus in order to measure serum color. Serum was prepared by keeping the blood at room temperature for 15 min until coagulation, and then centrifuged (3,000 g for 10 min). Samples of 200 μL of serum from the birds were transferred to a transparent 96-well plate (Greiner Bio-One, Kremsmünster, Austria) and their absorption spectra were acquired using an Infinite M200 spectrophotometer (Tecan, Männedorf, Switzerland) between 300 and 572 nm (2 nm steps).

Experiment 2. Birds (chickens) from generation 21 (N=192 D+, 192 D−) were produced in two successive hatches. The birds were fed with the alternative diet tested in experiment 1 (Table 1). They were reared on the floor from hatch to 13 day (13 d) and then transferred to individual cages for a balance trial. The balance trial was done between 21 and 23 days (21 and 23 d) and the animals were blood sampled at 24 day (24 d). The birds were weighed at 21 and 23 days. The procedures for the balance trial, feces treatment, blood samples treatment, and serum color measurements were the same as in experiment 1. The absorbance of the serum was measured every 2 nm between 342 and 572 nm.

Phenotypic and Genetic Analyses

In order to test the effect of the new diet on digestive efficiency, AMEn data from experiment 1 were analyzed with the GLM procedure from SAS® 9.4 (SAS Institute, Cary N.C.), including the fixed effects of line, diet and line by diet interaction.

Absorbance differences between D+ and D− were tested on the serum color data of animals fed with Rialto diet of experiment 1 with a Welch test every 2 nm from 300 to 578 nm (Welch, 1947).

For genetic analyses, all available data from each generation of selection of D+ and D− lines were included, i.e. 4,626, 5,068, and 417 animals for AMEn, body weight at 23 d, and serum color, respectively. Regarding serum color, we used the absorbance data gathered every 2 nm between 342 and 572 nm from experiments 1 and 2. Genetic analyses were performed using VCE6.0 (Neumaier and Groeneveld, 1998; Groeneveld et al., 2010). We applied an animal model including the fixed effects of hatch (N=28), rearing cell (N=8), and sex. For serum color, a fixed effect of plate (N=6) was also included. The pedigree file included a total of 6,376 animals. Taking into account the large number of traits and the high correlation between absorbance variables at neighboring wavelengths, we made a series of analyses including each AMEn, body weight at 23 d, and absorbance of serum at 2 different wavelengths. All possible combinations between the two different wavelengths were tested, leading to a total of 276 analyses. The results presented below are the mean values of genetic parameters and of their standard errors obtained for each separate analysis.

Results and Discussion

Phenotypic Results on Experiment 1

Analysis of data from experiment 1 showed that the AMEn difference between the D+ and D− lines was in the same range with the two diets (424 and 501 kcal·kg$^{-1}$ DM with the Rialto and alternative diets, respectively). The new diet is as difficult to digest as the initial one, AMEn values being 4.7% lower than with the initial diet (Table 2).

TABLE 2

Analysis of variance of line and diet effect on AMEn in experiment 1

|  | D+ | D− |
| --- | --- | --- |
| N | 40 | 40 |
| LSMEANS with Rialto diet | 3,478 | 3,054 |
| LSMEANS with alternative diet (kcal.kg$^{-1}$ DM) | 3,361 | 2,860 |
| SEM (kcal.kg$^{-1}$ DM) | 68 | |
| P (line effect) | <0.0001 | |
| P (diet effect) | 0.03 | |
| P (line × effect) | 0.58 | |

Briefly, D+ and D− serum color was significantly different between 430 and 516 nm, and indicated a more colored serum from the D+ line (FIG. 1). By 'more colored serum' it means a more intense colored serum (intense yellow). The most significant difference was found at 492 nm, which corresponds to the region of carotenoid absorption, especially lutein and zeaxanthin (Rodriguez-Amaya, 2001) which are the major carotenoids present in cereal grains, particularly wheat (Abrar et al., 2015). Moreover, as lutein and zeaxanthin are better absorbed by chickens than other carotenoids present in this spectral zone, such as γ-carotene, astaxanthin or cryptoxanthin (Surai et al., 2001), we can expect that this peak of absorbance at 492 nm is likely to correspond to lutein and zeaxanthin.

Genetic Parameters of Serum Color

Heritability estimates of AMEn and body weight (BW) were moderate to high (0.36±0.02 and 0.50±0.04, respectively). The genetic correlation between AMEn and BW was not significant (0.09±0.06). The estimates are consistent with previous estimates obtained from these lines (Mignon-Grasteau et al., 2004).

Heritability estimates of serum color (Table 3) were low and not significant at the lowest (342 to 432 nm) and highest (512 to 572 nm) wavelengths. Estimates between 462 and 502 nm were moderate (between 0.24 and 0.31) and significantly different from 0, with a maximum heritability at 492 nm.

TABLE 3

Genetic parameters (±standard errors) for serum color.

| Absorbance at wavelength | Heritability | Genetic correlation with | |
| --- | --- | --- | --- |
|  |  | AMEn | BW |
| 342 nm | 0.08 ± 0.07 | 0.52 ± 0.61 | 0.75 ± 0.26 |
| 352 nm | 0.09 ± 0.07 | 0.54 ± 0.46 | 0.73 ± 0.25 |
| 362 nm | 0.10 ± 0.09 | 0.58 ± 0.45 | 0.69 ± 0.28 |
| 372 nm | 0.10 ± 0.09 | 0.62 ± 0.44 | 0.70 ± 0.27 |
| 382 nm | 0.10 ± 0.14 | 0.68 ± 0.46 | 0.66 ± 0.45 |
| 392 nm | 0.11 ± 0.08 | 0.78 ± 0.32 | 0.57 ± 0.25 |
| 402 nm | 0.13 ± 0.07 | 0.92 ± 0.16 | 0.43 ± 0.27 |
| 412 nm | 0.12 ± 0.08 | 0.97 ± 0.15 | 0.31 ± 0.48 |
| 422 nm | 0.13 ± 0.07 | 0.97 ± 0.10 | 0.25 ± 0.28 |
| 432 nm | 0.18 ± 0.08 | 0.90 ± 0.18 | 0.32 ± 0.24 |
| 442 nm | 0.20 ± 0.16 | 0.83 ± 0.48 | 0.36 ± 0.37 |
| 452 nm | 0.26 ± 0.18 | 0.85 ± 0.41 | 0.33 ± 0.47 |
| 462 nm | 0.28 ± 0.10 | 0.81 ± 0.23 | 0.30 ± 0.24 |
| 472 nm | 0.27 ± 0.09 | 0.82 ± 0.22 | 0.32 ± 0.20 |
| 482 nm | 0.28 ± 0.09 | 0.82 ± 0.23 | 0.32 ± 0.22 |
| 492 nm | 0.31 ± 0.09 | 0.84 ± 0.28 | 0.29 ± 0.27 |
| 502 nm | 0.24 ± 0.12 | 0.76 ± 0.30 | 0.37 ± 0.24 |
| 512 nm | 0.16 ± 0.08 | 0.65 ± 0.54 | 0.51 ± 0.25 |
| 522 nm | 0.13 ± 0.16 | 0.55 ± 0.44 | 0.58 ± 0.36 |
| 532 nm | 0.11 ± 0.07 | 0.60 ± 0.43 | 0.61 ± 0.26 |
| 542 nm | 0.11 ± 0.09 | 0.71 ± 0.72 | 0.60 ± 0.30 |
| 552 nm | 0.11 ± 0.07 | 0.69 ± 0.36 | 0.61 ± 0.26 |
| 562 nm | 0.11 ± 0.07 | 0.61 ± 0.41 | 0.62 ± 0.26 |
| 572 nm | 0.11 ± 0.07 | 0.75 ± 0.29 | 0.60 ± 0.24 |

Figure 2:
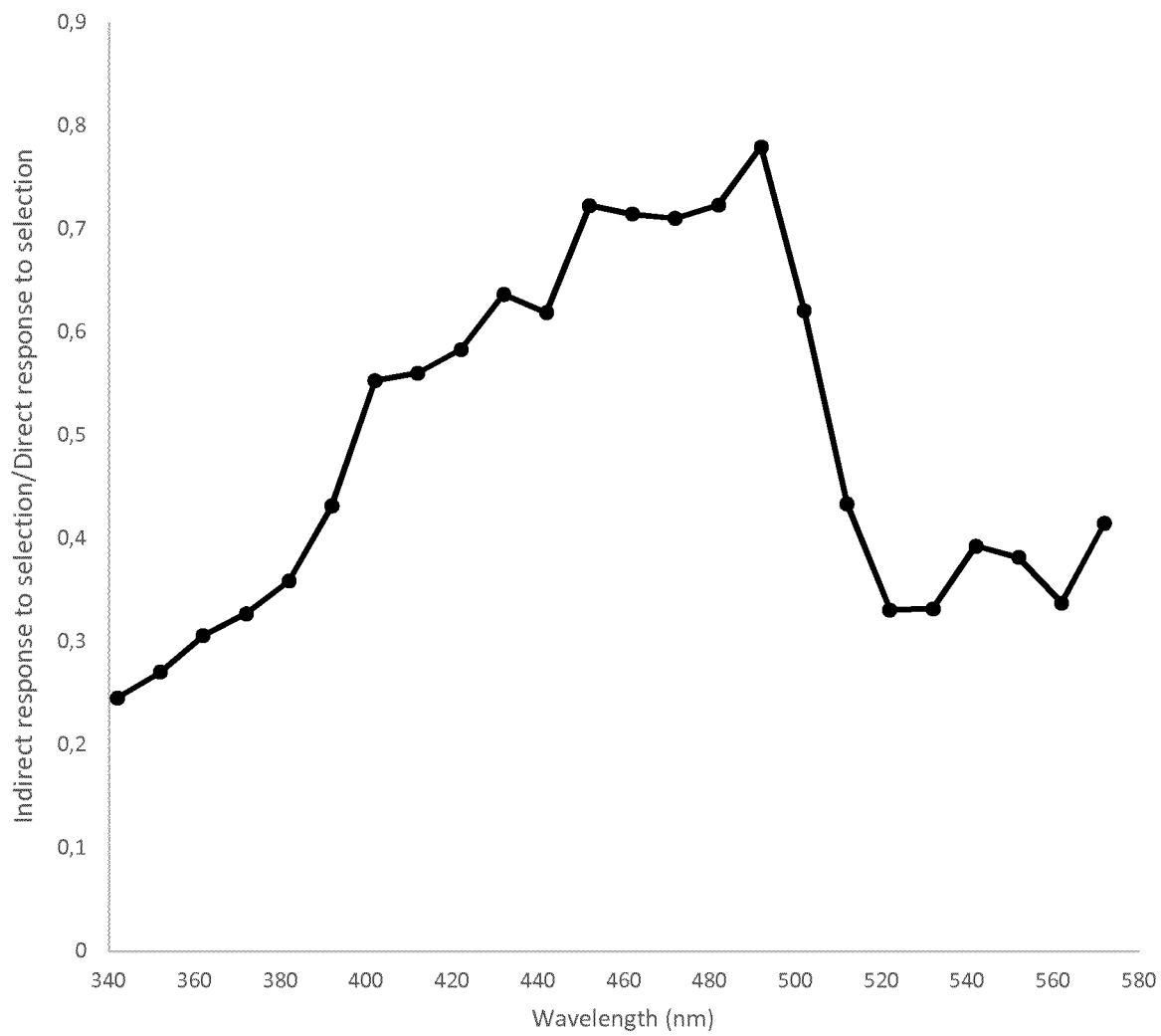
FIG. 2. Ratio of the expected response of AMEn to indirect selection of serum color to the expected response of AMEn to direct selection.

These estimates are close to the heritability of carotenoid concentration in 8-week-old broilers (0.20 to 0.32) obtained in prior studies (Stone et al., 1971; Washburn and Ruff, 1978). The genetic correlations between AMEn and serum color were the highest (0.76 to 0.97) for wavelengths between 392 and 502 nm. By contrast, in the same zone, genetic correlations between serum color and body weight were low and not significant. Taking into account heritability and genetic correlation estimates, serum absorbance at 492 nm would be the most efficient indirect criterion of selection for AMEn, and would lead to an indirect response estimated at 78% of the response of AMEn to direct selection (FIG. 2).

Carotenoids concentration in the serum is highly dependent on the capacity of the animal to absorb them from the diet. Carotenoids absorption is affected by intestinal pH and fiber content of the diet (Faure et al., 1999). In our case, it has been shown that intestinal pH differs between both lines (de Verdal et al., 2010), and we are using a diet with a high fiber content, which can thus affects carotenoids absorption. Moreover, the link between digestive efficiency and carotenoid content can also be explained by the indirect consequences of selection on digestive efficiency.

Our experiments on these divergent lines showed that this selection affected not only digestion, but also structure of the intestine and immune system. Indeed, carotenoids are involved in the structure of intestine through their role in the operation of gap junctions between epithelial cells of the intestine (Faure et al., 1999) and in immune system as they enhance cell-mediated and humoral immune response (Chew and Park, 2004).

Taking into account its ease of measure, its level of heritability and its genetic correlation with digestive efficiency, serum color seems to be a promising indirect criterion for selecting digestive efficiency (DE) of poultry, to be used in selection schemes to improve digestive efficiency.

REFERENCES

Abrar, H., Larsson, H., Kuktaite, R., Olsson, M. E., and E. Johansson. 2015. Carotenoid content in organically produced wheat: relevance for human nutritional health on consumption. Int. J. Environ. Res. Public Health 12:14068-14083.

Bastianelli, D., Bonnal, L., Juin, H., Mignon-Grasteau, S., Davrieux, F., and B. Carré. 2010. Prediction of the chemical composition of poultry excreta by near infrared spectroscopy. Near Infrared Spectrosc. 18:69-77.

Beauclercq S., et al., 2018. Relationships between digestive efficiency and metabolomics profiles of serum and intestinal contents in chickens. Scientific Reports: 8: 6678. DOI:10.1038/s41598-018-24978-9.

Bourdillon, A., Carré, B., Conan, L., Duperray, J., Huyghebaert, G., Leclercq, B., Lessire, M., McNab, J., and J. Wiseman. 1990. European reference method for the in vivo determination of metabolisable energy with adult cockerels: reproducibility, effect of food intake and comparison with individual laboratory methods. Br. Poult. Sci. 31:557-65.

De Verdal, H., Mignon-Grasteau, S., Bastianelli, D., Même, N., Le Bihan-Duval, E., and A. Narcy. 2013. Reducing the environmental impact of poultry breeding by genetic selection. J. Anim. Sci. 91:613-622.

Faure, H., Fayol, V., Galabert, C., Grolier, P., Le Moël, G., Steghens, J. P., van Kappel, A., and F. Nabel. 1999. Les caroténoïdes: 1. Métabolisme et physiologie. Ann. Biol. Clin. 57:169-183.

Garcia, V., Gomez, J., Mignon-Grasteau, S., Sellier, N., and B. Carré. 2007. Effects of xylanase and antibiotic supplementations on the nutritional utilisation of a wheat diet in growing chicks from genetic D+ and D− lines selected for divergent digestion efficiency. Animal 1:1435-1442.

Groeneveld, E., Kovac, M., and N. Mielenz. 2010. VCE user's guide and reference manual version 6.0. ftp://ftp.tzv.fal.de/pub/vce6/doc/vce6-manual-3.1-A4.pdf.

Mignon-Grasteau, S., Muley, N., Bastianelli, D., Gomez, J., Péron, A., Sellier, N., Millet, N., Besnard, J., Hallouis, J. M., and B. Carre. 2004. Heritability of digestibilities and divergent selection for digestion ability in growing chicks fed a wheat diet. Poult Sci. 83:860-867.

Neumaier, A., and E. Groeneveld. 1998. Restricted maximum likelihood estimation of covariances in sparse linear models. Genet. Sel. Evol. 1:3-26.

Rodriguez-Amaya, D. B. 2001. A guide to carotenoid analysis in foods. ILSI Press, Washington D.C., U.S.A.

Stone, H. A., Urban, W. E., and W. M. Collins. 1971. Blood carotenoid concentration, an estimate of its heritability and genetic relationship to body-weight in chicken. Poult. Sci. 6:1859-1862.

Surai, P. F., Speake, B. K., Sparks, N. H. C. 2001. Carotenoids in avian nutrition and embryonic development. 1. Absorption, availability and levels in plasma and egg yolk. J. Poult. Sci. 38:1-27.

Washburn, K. W., and M. D. Ruff. 1978. Genetic variability of carotenoid content in commercial broilers. Arch. Geflugelkd. 42:193-196.

Welch, B. L., 1947. The generalization of Student's problem when several different population variances are involved. Biometrika 34: 28-35.

The invention claimed is:

1. An in vitro method for evaluating digestive efficiency (DE) of poultry, by measuring color of a sample of liquid fraction of blood of said poultry.

2. The in vitro method of claim 1, wherein the sample of liquid fraction of blood is selected in the group consisting of plasma sample or serum sample.

3. The in vitro method of claim 1, wherein the sample of liquid fraction of blood is serum sample.

4. The in vitro method according to claim 1, wherein poultry is selected in the group consisting of chicken, hen, turkey, goose, duck, guinea fowl, quail and pigeon.

5. The in vitro method of claim 4, wherein poultry is chicken.

6. The in vitro method of claim 1, wherein the sample of liquid fraction of blood is a serum sample of chicken.

7. The in vitro method according to claim 1, wherein the color of a sample of liquid fraction of blood, is measured by absorption spectrum between 400 and 520 nm.

8. The in vitro method according to claim 1, wherein the samples of liquid fraction of blood, are placed in well plates and the absorption spectrum is measured with a spectrophotometer.

9. The in vitro method according to claim 1, wherein the samples of liquid fraction of blood are serum samples and the absorption spectrum is measured at 492 nm wavelength.

10. A method for selecting poultry having an improved digestive efficiency (DE) comprising the in vitro method for evaluating digestive efficiency (DE) of poultry by measuring color of a sample of liquid fraction of blood of said poultry.

11. The method according to claim 10, comprising a step of selecting poultry, having higher values of absorbance in serum sample at 492 nm wavelength.

12. A method for selecting feedstuffs or diets and/or producing feedstuffs or diets adapted and/or optimized for poultry comprising the in vitro method for evaluating digestive efficiency (DE) of poultry by measuring color of a sample of liquid fraction of blood of said poultry.

* * * * *

UNITED STATES PATENT AND TRADEMARK OFFICE
CERTIFICATE OF CORRECTION

PATENT NO. : 11,340,211 B2
APPLICATION NO. : 17/275987
DATED : May 24, 2022
INVENTOR(S) : Grasteau et al.

It is certified that error appears in the above-identified patent and that said Letters Patent is hereby corrected as shown below:

On the Title Page

At item (71) Line 5:
Delete "L'ENVIROMENT" and insert --L'ENVIRONNEMENT--

Signed and Sealed this
Twenty-fifth Day of June, 2024

Katherine Kelly Vidal
*Director of the United States Patent and Trademark Office*